(12) United States Patent
Svanberg et al.

(10) Patent No.: US 9,182,345 B2
(45) Date of Patent: Nov. 10, 2015

(54) APPARATUS AND METHOD FOR NON-INTRUSIVE ASSESSMENT OF GAS IN PACKAGES

(71) Applicant: GasPorOx AG, Lund (SE)

(72) Inventors: Sune Svanberg, Lund (SE); Anders Johnsson, Malmö (SE); Märta Lewander, Lund (SE); Annika Olsson, Lund (SE)

(73) Assignee: GasPorOx AB, Lund (SE)

( * ) Notice: Subject to any disclaimer, the term of this patent is extended or adjusted under 35 U.S.C. 154(b) by 119 days.

(21) Appl. No.: 14/152,778

(22) Filed: Jan. 10, 2014

(65) Prior Publication Data

US 2014/0125970 A1 May 8, 2014

Related U.S. Application Data

(63) Continuation of application No. 13/320,197, filed as application No. PCT/EP2010/056511 on May 11, 2010, now Pat. No. 8,638,439.

(60) Provisional application No. 61/213,145, filed on May 11, 2009.

(51) Int. Cl.
*G01N 21/59* (2006.01)
*G01N 21/17* (2006.01)
*G01N 21/3504* (2014.01)

(52) U.S. Cl.
CPC ............ *G01N 21/59* (2013.01); *G01N 21/1702* (2013.01); *G01N 21/3504* (2013.01)

(58) Field of Classification Search
USPC ........................................................ 356/437
See application file for complete search history.

(56) References Cited

U.S. PATENT DOCUMENTS

| 5,155,019 A | 10/1992 | Sussman et al. |
| 5,473,161 A | 12/1995 | Nix et al. |
| 5,753,797 A | 5/1998 | Forster et al. |
| 6,639,678 B1 | 10/2003 | Veale |

(Continued)

FOREIGN PATENT DOCUMENTS

| EP | 1906169 A1 | 4/2008 |
| JP | 2007508567 A | 5/2007 |

(Continued)

OTHER PUBLICATIONS

United States Patent and Trademark Office, Notice of Allowance mailed Sep. 23, 2013 in U.S. Appl. No. 13/320,197, 8 pages.

(Continued)

*Primary Examiner* — Tu Nguyen
(74) *Attorney, Agent, or Firm* — Inskeep IP Group, Inc.

(57) ABSTRACT

A method and apparatus are disclosed for assessment of a sealed package. Light is emitted from a narrow-band laser source towards said package from outside of said package. An absorption signal of said light scattered in said package is measured, wherein said absorption is caused by said at least one gas when said light is scattered and travels in said sealed package. Measuring is made outside of said package, whereby said assessment is non-intrusive with regard to said package. It is determined if a deviation exists from a predetermined, expected gas composition and/or concentration of said at least one gas within said sealed package based on said measured absorption signal. Thus sealing of said package for said gas is detected.

22 Claims, 4 Drawing Sheets

(56) References Cited

U.S. PATENT DOCUMENTS

| | | | |
|---|---|---|---|
| 7,887,752 B2 | 2/2011 | Heiner et al. | |
| 2003/0132389 A1* | 7/2003 | Von Drasek et al. | 250/343 |
| 2008/0123712 A1* | 5/2008 | Zhou et al. | 372/55 |
| 2008/0255769 A1* | 10/2008 | Zhou et al. | 702/24 |
| 2009/0059218 A1 | 3/2009 | Harner et al. | |

FOREIGN PATENT DOCUMENTS

| | | |
|---|---|---|
| JP | 2008083049 A | 4/2008 |
| WO | WO 2005/040753 A2 | 5/2005 |

OTHER PUBLICATIONS

United States Patent and Trademark Office, Office Action mailed Jun. 3, 2013 in U.S. Appl. No. 13/320,197, 12 pages.

WIPO, European International Search Authority, International Search Report and Written Opinion mailed Nov. 23, 2010 in International Patent Application No. PCT/EP2010/056511, 11 pages.

Lewander, M. et al., "Food monitoring based on diode laser gas spectroscopy," *Appl Phys B* (2008) 93: 629-625, Sep. 30, 2008, 7 pages.

Japanese Patent Office, Office Action mailed Jun. 17, 2014 (translation) in Japanese Patent Application 2012510281, 2 pages.

\* cited by examiner

APPARATUS AND METHOD FOR NON-INTRUSIVE ASSESSMENT OF GAS IN PACKAGES

RELATED APPLICATIONS

This application is a continuation of U.S. patent application Ser. No. 13/320,197 filed Feb. 23, 2012 entitled Apparatus And Method For Non-Intrusive Assessment Of Gas In Packages, which is the U.S. National Phase of and claims priority to International Patent Application No. PCT/EP2010/056511, International Filing Date 11 May 2010, entitled Apparatus And Method For Non-Intrusive Assessment Of Gas In Packages, which claims priority to U.S. Provisional Application Ser. No. 61/213,145 filed 11 May 2009 entitled Arrangement And Method For Non-Intrusive Assessment Of Gas In Packages, all of which are hereby incorporated herein by reference in their entireties.

FIELD OF THE INVENTION

This invention pertains in general to the field of assessment of packages, and in particular of gas compositions in packages, such as sealed packages including a gas volume. More precisely the invention relates to non-intrusive assessment of gas in food packages.

BACKGROUND OF THE INVENTION

In modern society, the trend among consumers to prefer fresh products leads to that chilled food is more and more competing with frozen and ambient counterparts. Fresh or chilled food is more sensitive, thus enhancing the demand from food consumers to be able to trust that the food they buy and consume is safe. One important issue in the transfer from ambient or frozen food products to chilled food is therefore the issue of safety and quality which is identified as an increasing concern, emphasized frequently in industry and media.

The demand for fresh chilled food has created a need for distribution of fresh products around the year. Fresh and chilled foods require both quicker distribution due to shorter shelf life, and better product and package integrity due to safety and quality issues at the point of consumption. The two most important factors concerning the shelf life are time and temperature. Most of the deteriorating changes that take place in food are temperature dependent and occur at a slower rate at lower temperatures. In addition to the time and temperature parameters, the natural presence of oxygen in food products and packaging environments, hastens chemical breakdown and microbiological spoilage of food. Traditional packaging methods are therefore largely being replaced by newer techniques where other gases than oxygen are filled in the package headspace. Modified Atmosphere Packaging (MAP) is one example of such techniques, used to reduce the oxygen content and to prolong the shelf life of the product it contains.

Due to food deteriorating aspects, the food handling, preservation and packaging have become important aspects of great public interest and concern. The MAP technology theoretically meets the new consumer requirements of prolonged shelf-life for chilled or fresh products, and the MAP packaging concept is growing in importance in the food packaging market. The main benefit of MAP is argued to be the reduction of indirect costs due to less product waste. But with the increased quality and safety concerns, the importance to be able to assess the status of packed food to ensure its quality and suitability for consumption must also be stressed. Many sensing techniques have been developed; however, most of them destroy the packaged sample and thereby cause waste of both products and packages. E.g., gas chromatography and other sampling techniques require puncturing the package for gas extraction, while measurement techniques should preferably be non-intrusive in nature, in order to maintain packaging integrity and reduce waste of samples.

Modified Atmosphere Packaging

Oxygen is a very reactive gas, naturally present in air. Most packaged food items come with a natural headspace of air between the product and the package. Oxygen is thus frequently present in the headspace. Due to the high activity of this molecule, it is important to control its concentration in order to secure quality and increase shelf-life of the product. Generally, it is desirable to reduce its concentration from ambient (21 percent) to a few percent or to a completely oxygen-free environment. By replacing the oxygen in the headspace the oxidative processes are reduced and the shelf life of the food product is extended.

In order to reduce the natural concentration of oxygen in air, food products are packaged in modified or controlled atmosphere. Modified atmosphere packaging (MAP), as used in this disclosure, is defined by Hintlian and Hotchkiss as "the packaging of perishable product in an atmosphere which has been modified so that its composition is other than air". In MAP the natural oxygen content inside the package is replaced with other gases such as carbon dioxide ($CO_2$) or nitrogen ($N_2$). Frequently, the gas composition is actively changed at the time of packaging, either by flowing gas during the packaging or by first subjecting the product to vacuum followed by inlet of the desired gas mixture.

Fresh products such as fruits or cured meat are the most common products to pack in modified atmosphere. But more frequently, products such as high quality fruit juices are packed in modified atmosphere in order to reduce deterioration from oxidation and to extend the product shelf-life. The modified atmosphere is slowing chemical and biochemical deteriorative processes as well as slowing or preventing the growth of spoilage organisms. For high quality fruit juices, nitrogen is the most common gas to use in the headspace for replacement of oxygen. Nitrogen is an inert gas and does not dissolve well in water or lipids and thus ensures that a package looks filled and is not collapsing. It has no anti-microbial activity but by displacing oxygen in the headspace of packages the oxidative processes of the products are delayed.

For MAP, the package integrity and tightness are necessary to maintain the correct composition of gas inside the package, thus securing that no gas exchange takes place between the package and its environment. It is important to control the oxygen permeability in order to secure the prolonged shelf life of liquid food products, such as for example high quality orange juice. Packages with a modified atmosphere therefore require packaging materials that are tight to gas transfers, in order to avoid oxygen from getting into the headspace. For packages that have an exchange, (intended or not intended) with the outside environment, equilibrium will be reached between the inside and outside of the package over time with oxygen entering the headspace. Furthermore, in a modified atmosphere package, equilibrium of gas concentrations inside the package may arise due to the interaction between the product and the gas contained in the package. A measurement method or apparatus is desired for assessing the sealing tightness of the packaging. Such method or apparatus is for instance suitable to detect the headspace gas composition that will include the simultaneous gas movement from permeation and through the exchange from product to headspace, in a dynamic MAP system.

Non-Intrusive Gas Sensing of Food Packages

Measurement of oxygen contents in sealed packages might be the most pertinent aspect of monitoring the gas composition in the headspace of packages. Oxygen assessment can be made by performing optical measurements, using small sensor disks prepared to change in colour in the presence of oxygen. Alternatively and more commonly used, the sensor disk is prepared with a ruthenium- or platinum-containing dye, with fluorescence properties that decreases with the amount of oxygen. However, these techniques are intrusive from the point of view that the small disks have to be introduced in the package at the time of sealing. In addition there is a cost and a safety aspect ensuring that the active reactive agent does not influence the product or the consumer. Hence, an alternative non-intrusive method or apparatus would be advantageous.

From a safety and consumer perception aspect, non-intrusive measurements, without devices put on or inside the package are therefore called for. In addition all extra items incur an extra cost, in terms of direct costs and indirect costs such as extra handling time, machine investments etc. Non-intrusive measurements also allows for measurements over time for packages during its entire shelf life.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a method and an apparatus according to the appended patent claims.

According to a first aspect of the invention a method is provided for assessment of a sealed package. The method comprises emitting light from a narrow-band laser source towards the package from outside of the package; measuring an absorption signal of the light scattered in the package, said absorption caused by at least one gas in said package when the light is scattered and travels in the sealed package. The measuring is made outside of the package, and the assessment is non-intrusive with regard to the package. The assessment is based on determining if a deviation exists from a predetermined, expected gas composition and/or concentration of the at least one gas within the sealed package based on the measured absorption signal.

According to a second aspect of the invention an apparatus is provided for assessment of a sealed package. The apparatus comprises two narrow-band laser sources adapted to emit light toward the package from outside of the package, and a light detector adapted to measure absorption signal of the light scattered in the package. The absorption is caused by the at least one gas when the light is scattered and travels in the sealed package. The measuring is made outside of the package, and the assessment is non-intrusive with regard to the package. The apparatus further includes a control unit adapted to determine if a deviation exists from a predetermined, expected gas composition and/or concentration of the at least one gas within the sealed package based on the measured absorption signal.

Further embodiments of the invention are defined in the dependent claims, wherein features for the second and subsequent aspects of the invention are as for the first aspect mutatis mutandis.

Some embodiments provide for non-intrusive determining of a gas concentration in a sealed package, and if a deviation exists from an expected concentration or a deviation from a ratio between gas concentrations or absorption signals. The ratio between the absorption of an unknown gas with the absorption of a reference gas, e.g. water vapour, provides information about the measurement gas.

Some embodiments provide for remote assessment of a gas inside a sealed package.

Some embodiments provide for determining of the concentration of a gas in a sealed package which is translucent. To be able to use the method the package or sample need to be translucent, meaning that emitted light must be able to travel into the gas and interact with it and then out again. The package can appear non-transparent to the naked eye, but laser light might still be able to travel through it in a specific translucent wavelength window of the laser light. Embodiments provide for assessing information of gas inside packages, which are made of a material that is non-transparent, but translucent.

Some embodiments provide for assessment of gases inside sealed food packages having been sealed with modified atmosphere packaging (MAP), controlled atmosphere (CAP), or a unique composition of a gas.

Some embodiments provide for determining sealing tightness of a sealed package over time.

Some embodiments provide for determining if a sealed package has been sabotaged.

Some embodiments provide for determining if the product inside a sealed package is the product originally packaged in the sealed package.

Some embodiments provide for assessment of sealed packages in line with a product manufacturing chain devised for packaging of products in the sealed packages.

Some embodiments provide for assessment of sealed packages in a handheld compact apparatus.

Gas absorption spectroscopy is an alternative gas sensing method for food packages, interesting since it can provide non-intrusive, real-time measurements without the need to add sensors inside the packages. The technique is based on the fact that each molecule absorbs light in a unique way, making them possible to identify and quantify with absorption spectroscopy. A limitation of its conventional implementation is the need of a transparent package and headspace.

In 2001 an alternative approach of gas absorption spectroscopy, named GASMAS (GAs in Scattering Media Absorption Spectroscopy) was presented, enabling sensing of gas surrounded by scattering media. The principle of GASMAS is that the spectrally sharp gas absorption can be distinguished from the broadband absorption of liquids and solids. This results in that a small gas absorption signal, (order of 1 in 10 000) can be extracted from light passing through a scattering and absorbing material despite transmitting only a minor fraction of the injected light with the GASMAS method. However, GASMAS was hitherto not known for the present field of assessment of packages as defined by embodiments described herein.

In certain embodiments, the GASMAS technique allows thus for assessment of packages made of non-transparent, scattering materials that are surrounding a gas space inside the package or the food product.

It is disclosed a non-intrusive sampling technique, for quality assurance in the liquid food packaging industry. The GASMAS technique opens for analysis of gases inside natural products, such as different kinds of food where strong light scattering often makes the application of conventional gas spectroscopic techniques difficult.

With GASMAS gas located in cavities inside products, such as different food items, e.g. meat, bread, fruit and liquids, as well as different scattering packaging materials, such as plastic and paper, can be analysed optically for the first time non-invasively. This means that gas inside headspace of packages that are non-transparent, but translucent (i.e. not see through to the eye, but possible for light to penetrate through although not in a straight manner) can be analyzed.

In some embodiments, a simultaneous monitoring of oxygen and water vapour is provided for the headspace of non-transparent, but translucent packages with a modified atmosphere, using the above described GASMAS technique.

Due to the scattering of the light in the sample a complication at the evaluation of the absorption signals obtained with the GASMAS method is the unknown gas interaction path length which the light has experienced. The path length is important in traditional gas absorption spectroscopy for concentration quantification, as determined by the Beer-Lambertian law.

A solution to the conundrum with unknown gas interaction path length is to simultaneously probe a reference gas of known concentration in the same volume as the measurement gas. This is enabled by using a second laser at a wavelength close to the first laser. By forming the ratio of the gas absorption signal of the measuring gas and the reference gas a quantity proportional to the concentration of the measuring gas is obtained. Water vapour has been shown to be a feasible reference gas due to its saturation point at room temperature. In an enclosing with liquid water present, the concentration of water vapour, only dependent of the temperature, is known.

Oxygen is of major importance for this application and water vapour is monitored as a reference gas to enable oxygen concentration evaluation.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION OF EMBODIMENTS OF THE INVENTION

Figure 1:
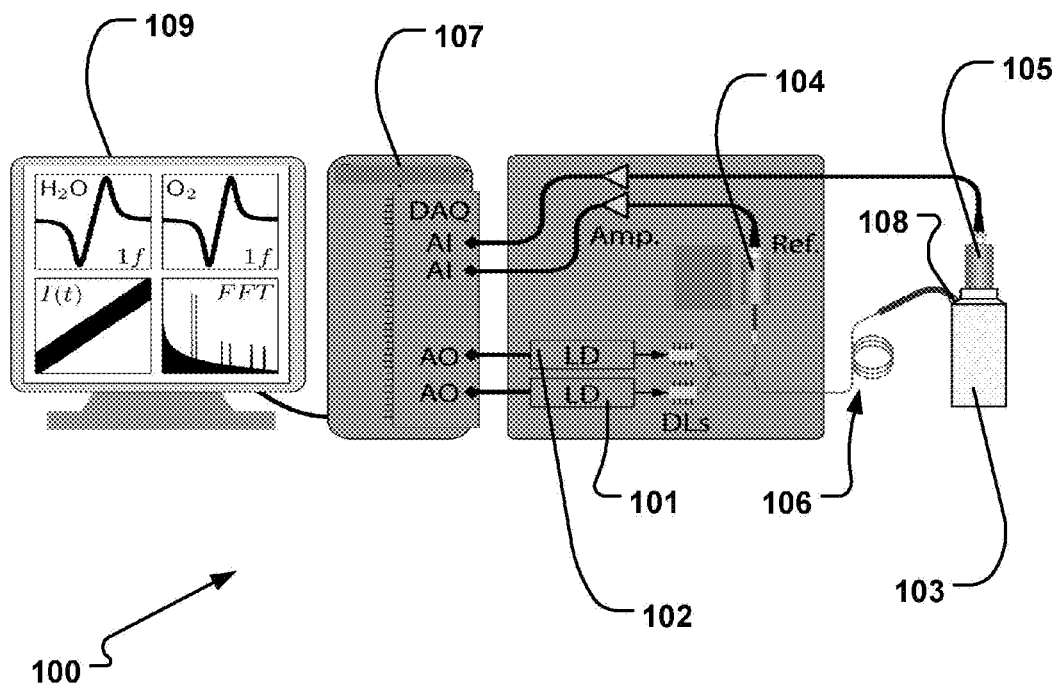
FIG. 1 is a schematic illustration of a gas sensing instrument according to an embodiment of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

In a specific embodiment, a liquid inside a package is orange juice. However, in other examples, embodiments or applications, the liquid inside the package maybe another foodstuff, such as for instance apple juice, cranberry juice, dairy products such as yoghurt, milk, soup, vegetables, soft drinks, wine, prepared foods, poultry or other meat products, preserved provisions that traditionally were stored as canned goods but thanks to advancements in modern packaging technology are storable in multilayer packaging material that is translucent as discussed herein. In other examples, embodiments or applications, the packaged material contained in the package may be solid, and/or comprise solid particles, such as yoghurt with fruit pieces, juice with pulp, etc. In some embodiments or examples, the package is not sealed.

The possibility to assess information about the gas composition non-intrusively has been illustrated on a gable top carton package for milk, with a non-modified atmosphere, i.e. air headspace, see Ref. 1, which is incorporated herein by reference in its entirety for all purposes. In the present disclosure the method is used on series of carton packages for fresh orange juice packed in a modified atmosphere of nitrogen. Three series of high quality orange juice packaged in flexible carton packages under modified N2 atmosphere and with different storage time, have been measured with aspect of their gas composition.

Three sample sets of orange juice packages, with different expiration dates were analysed. Each set consisted of 20 samples.

Measurement Apparatus Setup

The gas sensing instrument 100 used is depicted in FIG. 1, and consists of two diode lasers drivers 101, 102, (DFB Nanoplus) monitoring oxygen and water vapour inside food packages 103. The light from the diode lasers (DLs) is brought together and separated into two fibres—one used to monitor the background (Ref.) and one sent to the sample (Probe), with reference 104 and probe 105 detector respectively. The two diode lasers operate at the wavelengths 760 nm and 935 nm, were the food package and the orange juice are translucent, making the GASMAS technique suitable. The laser light is guided to the sample 103 via optical fibres 106 and a hand held fibre head 108. The scattered light emerging out from the sample is acquired by a hand held 10×10 mm detector (Hamamatsu S3590-01) and the generated signal is sampled by a computer 107. The computer is equipped with a special data acquisition card DAQ, making it possible to average the signals. Wavelength modulation techniques are used to increase the sensitivity of the instrument by sinusoidally modulating the wavelength at about 10 kHz and studying the generated harmonics. Simultaneous detection of water vapour and oxygen is enabled by modulating at different frequencies. In this embodiment the first overtone ($1f$) illustrated on the monitor 109 in FIG. 1, was used for absorption evaluation. Detailed technical description, system performance and data evaluation is presented in Ref. 4, which is incorporated herein by reference in its entirety for all purposes. However, Ref. 4 is on a completely different field of technology, namely medical devices for measurement of gas inside the sinus cavities. It is important to note that the light transducer and detector were hand held and not entirely fixed. In GASMAS complete fixation of sample, light delivery and detector often lead to detrimental interference noise. Systematic ways of circumventing this includes dithering of laser beam and/or sample.

The gas signal obtained is referenced to a calibration measurement of 1000 mm of air, yielding a measure in the unit of mm, referred to as the Equivalent path length, Leq. This quantity is the distance the light has to travel in ambient air to experience the same gas absorption imprint. The absorption is governed by the Beer-Lambertian law and is dependent of both the species concentration and the distance over which the light interacts with the gas. Since the GASMAS technique studies scattered light, the gas interaction distance is unknown making it necessary to reference the absorption to a calibration measurement. The quantity obtained, Leq, is thus dependent on both the optical path length and the gas concentration. This means for example that a signal of 20% oxygen with an interaction distance of 25 mm or an absorption signal of 10% oxygen with an interaction distance of 50 mm gives the same Leq. However, by measuring water vapour, information about the sampling path can be obtained. A closed environment with liquid water is saturated giving a known water vapour concentration governed only by temperature. Using the equivalent path length, Leq, of water vapour as a measure of the interaction distance also for oxygen, results in the ratio of the oxygen and water vapour signals being proportional to the oxygen concentration. We here rely on the assumption that 760 nm and 935 nm laser light probe the same volume.

As an alternative to optical gas detection through observation of decreased light intensity due to gas absorption, acousto-optical detection can be used (See, e.g. Ref. 2, which is incorporated herein by reference in its entirety for all purposes). Then the narrow-band laser source is periodically shifted from an absorptive wavelength to a non-absorptive one. Collisional deexitation of laser-excited molecules leads to heat generation, i.e. increased gas pressure. When the laser is periodically tuned back and forth a periodic gas pressure wave is generated which can be detected, e.g. by an acoustic microphone (as a "tone" at the modulation frequency). Frequency- and phase-selective detection (lock-in detection) increases the signal-to-noise characteristics. Like in the GASMAS method, where light diffusely passing the gas and then being absorbed for correct laser tuning as detected by a reduction in light intensity reaching the optical detector, photoacoustic detection integrates the cumulative absorption experienced by the diffusing light.

Measurement Experience of Liquid Food Packages

Monitoring of gas inside packages has previously been demonstrated with the GASMAS technique on bake-off bread, packed minced meat and a gable top carton of milk, see Ref. 1, which is incorporated herein by reference in its entirety for all purposes. These early measurement were performed on single packages in order to illustrate the possibility to assess information about the gas inside sealed packages non-intrusively. The bake-off bread and the meat package were transparent or partly transparent and had a modified $CO_2$ atmosphere and non-modified atmosphere, respectively. Measurements were made non-intrusively through the product, while being inside the package. The result illustrated the possibility to access information about gas seated inside a packaged product.

The studied milk was packed in a non-transparent gable top carton package with non-modified atmosphere, i.e. a headspace of air. The results demonstrated that it is possible to determine the absorption of gas inside a headspace non-intrusively despite the fact that the package appears non-transparent. Both oxygen and water vapour were measured. When the package was perforated the ratio of oxygen and water vapour absorption signal remained constant. This fact demonstrates that the headspace oxygen concentration was originally the same as the ambient air. However, an increase in absorption was observed both in the oxygen and water vapour absorption signals following perforation. This phenomenon is interpreted as an effective path length increase due to movement of the sample when the perforation was performed. The observation illustrated the need to use simultaneous monitoring of water vapour as a reference in these types of measurements.

Measurements on Packages

In order to analyze the potential of the GASMAS technique as a food packaging quality control tool, large sample sets with non-transparent packages were used to obtain statistical data. Extract of oxygen concentration information in packages with a modified atmosphere headspace was investigated.

Figure 2:
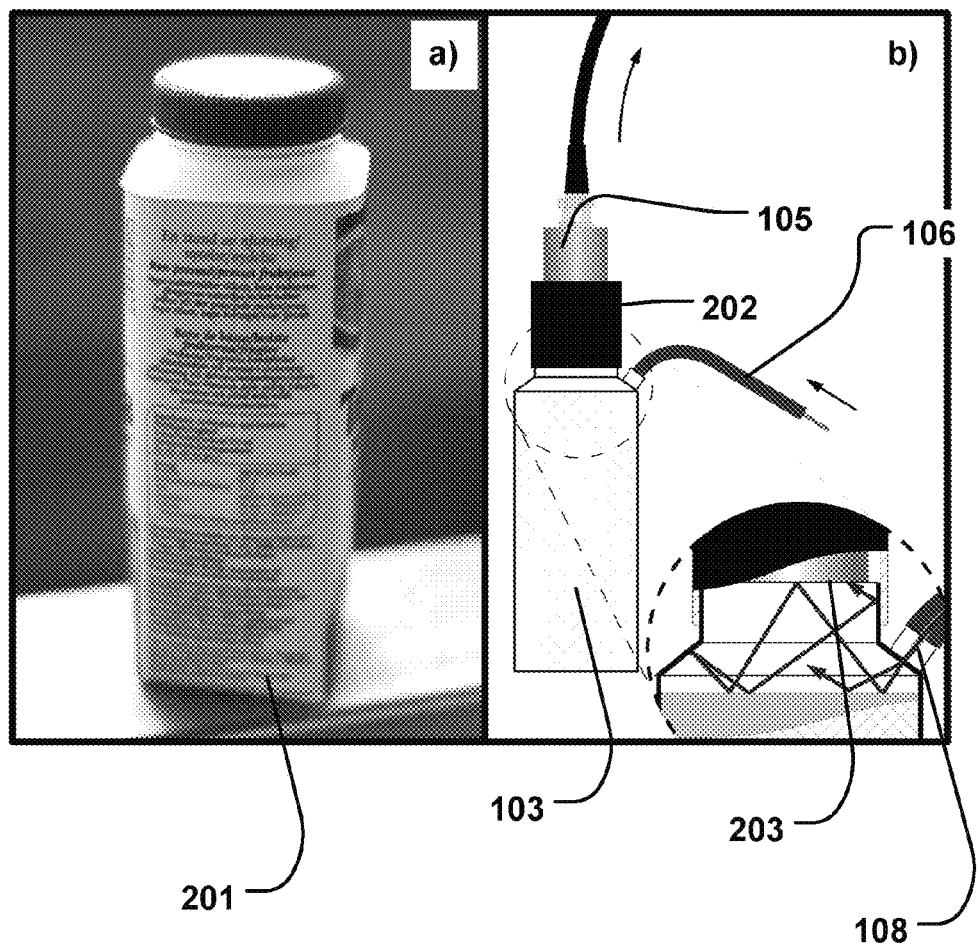
FIG. 2a shows a sample of the orange juice packages studied.
FIG. 2b shows an illustration of the detection geometry according to an embodiment of the invention.

Three sets of 20 packages of high quality orange juice, packaged in flexible carton portion packages 201 of 250 ml, with a plastic polyethylene (PE) top and a screw cap opening, were used for measurements; see FIG. 2a. The light is injected on the side of the plastic top and detected at the top of the package with the cap removed. Even with the cap removed, the package is still sealed by the moulded plastic top. The probe 105 may be provided with a thread corresponding to that of the (removed) cap for easy and reliable attachment to the package top.

The package 201 consists of a carton based sleeve made of printable paper coated with layers of polyethylene, and with an injection moulded plastic top of polyethylene. The headspace of the package is modified with nitrogen, $N_2$, in order to prolong the shelf life of the juice.

The purpose was to identify differences in the gas composition between the three sets with different shelf life. The sets were measured on Jan. 26, 2010 and had different expiration dates:

set 1: Oct. 30, 2008,
set 2: Aug. 22, 2009,
set 3: Feb. 23, 2010.

The laser fibre transducer 108 and the light detector 105 were hand held on the side and at the top of the plastic upper part of the package, respectively; see FIG. 2b. The cap was removed but the package was still intact due to the plastic oblate, the "tamper proof" that needs to be taken away before consumption. A shielding tube 202 of black paper was placed around the top of the package top 203 to prevent detection of leakage light passing from the fibre tip directly to the detector.

Alternatively, the absorption signal may be measured in non-contact mode remote from the sealed package. In an embodiment this may be done according to the principle disclosed in Ref. 3, which is incorporated herein by reference in its entirety for all purposes. In more detail, measurement of gas in a package may be made by a gas analysis setup using LIDAR multi-scatter techniques.

Each package was measured three times with repositioning of the laser fibre and detector to verify the reproducibility of the technique. The packages were refrigerated during the storage time but placed at room temperature one night before the experiment started. A uniform and known temperature condition for all packages, to ensure the possibility of calibration with water vapour was desired. Each package was weighed in order to identify any differences between samples and sets. To confirm the gas absorption signal originated from gas inside the package, and for absolute oxygen concentration calibration, one sample from each set was perforated with circular openings of 3 mm and measured with flow of nitrogen gas and with ambient air in the headspace.

Results

Figure 3:
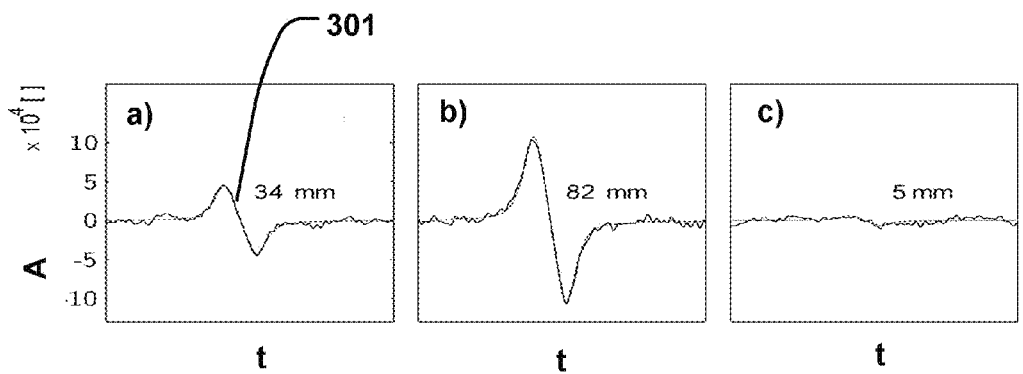
FIGS. 3a-c shows graphs of example signals of oxygen absorption from a package which is first intact (a), then punctured (b) and lastly flushed with nitrogen (c).

The perforation measurements on one package of each expiration date set showed that the absorption signal originated solely from the gas inside the headspace of the package. As nitrogen gas was flushed into the headspace the oxygen absorption signal basically disappeared. Further, the perforation experiment also verified that the headspace consisted of a modified atmosphere. Example absorption signals (A) from one package of the set with expiration date Feb. 23, 2010 are presented in FIG. 3 as function of time (t). Oxygen absorption 301 is shown from a package which is first intact (a), then punctured (b) and lastly flushed with nitrogen (c). The black curve is the measured signal and the grey curve a fitted ideal absorption imprint. The intact package gave an oxygen absorption signal of 34 mm. When puncturing the package the oxygen absorption signal increased, as the ambient air flowed into the package. Filling the headspace with nitrogen gas resulted in no oxygen signal, i.e. a signal lower than the noise background which for this case was equivalent to an Leq of 5 mm.

Figure 4:
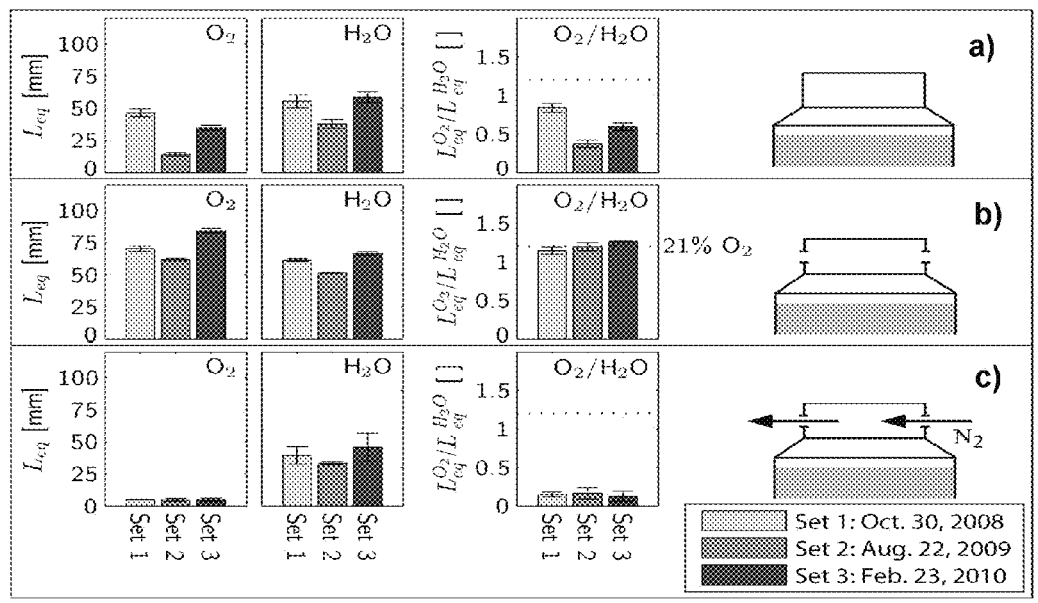
FIGS. 4a-c shows diagrams of the equivalent path length (Leq) of oxygen and water vapour as well as the ratio of oxygen and water vapour Leq for three packages from different expiration dates sets.

Similar results were obtained for the two other sets with other expiration dates when perforated, see FIG. 4 showing diagrams of the equivalent path length (Leq) of oxygen and water vapour as well as the ratio of oxygen and water vapour Leq for three packages from different expiration dates sets, for package which is first intact (a), then punctured (b) and lastly flushed with nitrogen (c). The presented values are averaged data of three measurements performed on each package together with the standard deviation. The oxygen absorption signal increased as the packages were perforated and decreased to the noise level as nitrogen was flushed into the headspace. The oxygen absorption signal level of the intact packages as well as the perforated package varied between the sets. Changes in gas interaction length, due to e.g., different filling levels, optical properties or measuring geometry, could explain such a variation in oxygen absorption signal. However, when forming the ratio of oxygen and water vapour Leq the discrepancies between the three samples remained for the intact packages, but equalized when the sample packages were perforated and ambient air filled the headspace. The three studied intact packages of different expiration dates can thus be proclaimed to have different amount of oxygen concentration. As noted, the ratio parameter for the perforated packages with ambient air in the headspace all equalized to a similar value, corresponds to 21 percent of oxygen concentration. Our observation suggests that the ratio of oxygen and water Leq can be used as an oxygen concentration measure. We here rely on that the water vapour signal is a measure of the probed path through the gas, which is possible under the condition of saturated humidity. Since small holes are made in the headspace the saturation of the enclosing is pertained.

An increase in water vapour signal was observed as the packages were perforated and is thought to be an effect of changed gas volume in the headspace. As the packages were being perforated it was noted that the top of the cap went from bulking inwards to becoming flat. The decrease in water vapour absorption signal as nitrogen gas is flushed through the headspace is believed to be an effect of an unsaturated gas volume due to flow of nitrogen. The ratio between the oxygen and water vapour absorption signal as an oxygen concentration measure is not feasible under such artificial conditions.

Figure 5:
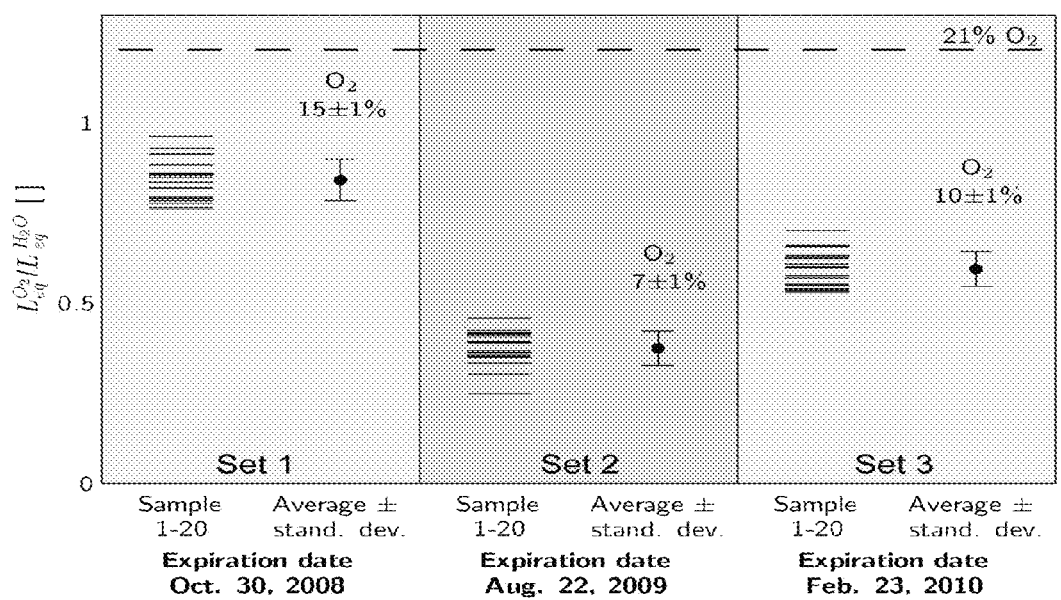
FIG. 5 shows diagrams of the ratio of the equivalent path length (Leq) of oxygen and water vapour for the intact packages of the three measured sets with different expiration dates.

The discrepancies in oxygen content, between the intact packages with different expiration dates were further analyzed by studying all the 20 samples of each expiration date. The ratio parameter, i.e. the measure of oxygen concentration was monitored, and the results are presented in FIG. 5 showing the ratio of the equivalent path length (Leq) of oxygen and water vapour for the intact packages of the three measured sets with different expiration dates. The presented data are averaged values of three measurements performed on each package and is presented to the left in each column. The average of all 20 measured samples together with corresponding standard deviation is presented to the right in each column.

No large variation was observed between the samples within one set, whereas a pronounced difference between the sets was obtained. Using the ratio value from the perforated packages as 21% oxygen to calculate corresponding concentration of the intact packages resulted in oxygen contents between 7-15% for the three studied sets. For the newly purchased packages, where the expiration date had not passed when the measurement were performed, an oxygen concentration of 10% with a standard variation of 1% between the 20 samples was obtained. For the older, expired, package sets a lower and higher oxygen concentration was measured, 7±1% and 15±1%, respectively. We note, that the oxygen content does not increase monotonously with storage time. This might indicate variations in sealing quality of the packaging machine(s). An alternative explanation could be that permeation through the package and/or through the exchange from product to headspace are in progress to different extent. Clear variation between the sets was not only measured in the ratio but also in the oxygen and water vapour Leq; see Table 1. Different sampling volume, due to scattering and absorption properties or filling variation between the sets could explain this behavior. However, the sample sets showed no large variations in weight, 275.4±0.9 g, 272.2±1.0 g and 272.4±0.3 g for set 1, set 2 and set 3, respectively.

Table 1 shows data obtained from 20 measured samples from each set with different expiration date. Oxygen and water vapour Leq and their ratio is presented as average ±standard deviation. Oxygen concentration is calculated using the ratio of perforated packages as 21 percent oxygen content.

TABLE 1

| Set | Exp. Date | $O_2 L_{eq}$ | $H_2O L_{eq}$ | $O_2 L_{eq}/H_2O L_{eq}$ | $O_2$ conc. |
|---|---|---|---|---|---|
| 1 | Oct. 30, 2008 | 46 ± 3 mm | 55 ± 5 mm | 0.84 ± 0.06 | 15 ± 1% |
| 2 | Aug. 22, 2009 | 14 ± 1 mm | 38 ± 3 mm | 0.38 ± 0.05 | 7 ± 1% |
| 3 | Feb. 23, 2010 | 35 ± 2 mm | 59 ± 4 mm | 0.60 ± 0.05 | 10 ± 1% |

The reproducibility test with three consecutive measures on each sample showed no large variation. The ratio parameter varied in average 3% between the measurements. A deviation of the ratio of 3% corresponds to a change in oxygen concentration of 0.45 percentage units (using 15% oxygen as obtained for set 1).

The oxygen concentration may be assessed by measuring the absorption signal (optically or photo-acoustically) for an intact package, followed by measurements in the same geometry on the same package for the two cases of a punctured package (yielding an ambient oxygen concentration of 21 percent) and a package flushed by nitrogen through the hole (s) made by puncturing the package (yielding a zero percent oxygen concentration). Subsequently a linear interpolation may be applied to derive the proper concentration value. The method then being applicable on intact packages of the same type in the same measurement geometry to non-intrusively assess the oxygen concentration, without the need of water vapour normalization, and corresponding accurate knowledge of package temperature.

In addition, temperature and pressure inside the package may be determined based on GASMAS. This makes the assessment in certain embodiments even more accurate and advantageous. For instance a measured temperature and pressure inside a package makes it very precise to determine a water vapour concentration inside the package.

The present disclosure clearly shows that the GASMAS method is highly suitable for monitoring of gases inside translucent non-transparent packages. Oxygen is of great interest for the modified atmosphere packaging industry since it is the reduction of oxygen that is sought for. An alternative gas to monitor is nitrogen, but this gas does not exhibit any absorption lines that can be studied with diode laser spectroscopy.

A requirement for gas monitoring with the GASMAS technique is that laser light must be able to travel through the sample, to some extent, and interact with the gas. In this disclosure about 0.1% of the incident laser light, i.e. 1 µW, was transmitted through the package and detected. It should be noted that the translucency of materials is different and varies with wavelength. For example metal films are not translucent at all and liquid water is only translucent below 1400 nm, i.e. in the visible and near infrared regime.

The GASMAS technique is of particular interest for the food packaging industry since it allows non-intrusive real-time gas monitoring of non-transparent packages. The main benefits of using non-intrusive measurements are the reduction of sample waste and that no extra costs in terms of extra sensors are added to each individual package.

Another value is the fact that it is possible to analyse the same sample at different points in time, i.e. over the entire shelf life of the product.

The measurements made in the present disclosure on modified atmosphere juice packages, illustrate the possibility to monitor the packed liquid food as well as the package integrity non-intrusively and over time for shelf-life measurements. This confirms the possibility to use GASMAS on carton based packages, as indicated in the initial tests made on single a gable top carton package for milk with ordinary air headspace. The present disclosure augments those results, firstly by showing good reproducibility and secondly by demonstrating the applicability to modified atmosphere packaging employing non-transparent packages. The use of normalization through water vapour monitoring to gain absolute oxygen concentration values is also demonstrated.

The results further indicate a potential for non-intrusive quality control of liquid food products and packages without waste of sample. The possibility to make such measurements non-intrusively indicates a future potential to introduce food quality measurements in the packaging production line as well as in the distribution chain, since the non-intrusive way of measuring allows for repeatable measures over time on the same sample. The quality control could certify the tightness of packages but also assess possible liquid food deterioration since it is possible to measure changes in gas composition over time.

A further aspect of food packaging testing is to ascertain that nobody has tampered or sabotaged the food package. Actually, recently several cases of sabotage of food packages have been reported. E.g., glass has been introduced in chicken packages, leading to the need to withdraw huge amounts of packed product. If someone has tampered with a package, e.g. for introducing contamination, the gas barrier would be broken and such a package would exhibit an anomalous gas composition. Even if MAP and CAP techniques have not been applied such tampering would be evident in the oxygen concentration, since the enclosed product will consume oxygen by oxidation.

The present invention thus also provides a solution to the non-intrusive monitoring of the intactness of food packages in the whole supply-chain, from the manufacturer via the distributor(s) to the local grocery stores.

The above technique using MAP or CAP may also be used in other industries than food packaging, e.g. to ensure that the product inside a sealed package is indeed the original product. This is very useful for industries having problems with counterfeit and illegally-copied goods such as drugs or medicine, clothes, garments, mobile communication apparatus such as mobile telephones, watches, optical discs such as CDs or DVDs, memory circuits, microprocessors, integrated circuits, or medical devices.

Instead of using MAP or CAP a unique composition of gas may be used to uniquely detect the manufacturer of the goods and/or the product. This unique composition is detectable by embodiments of the present invention. According to a study of Counterfeiting Intelligence Bureau (CIB) of the International Chamber of Commerce (ICC), counterfeit goods could make up as much as 5 to 7% of world trade.

Alternatively, a shelf life of packaged goods may be determined based on a gas inside a package, detectable by embodiments of the present invention. For instance medical devices may be packaged in a sterile environment. For example surgical tools may be positioned in a correspondingly recessed plastic molding thereof, and packaged in a specific gas atmosphere for sterility. Shelf life ends when the gas atmosphere no longer is reliably kept by the package, e.g. after six or nine months. Thanks to measuring the gas composition inside the package, the shelf life may be extended when gas inside the sterile package is measured and still a sufficient gas atmosphere is detected by embodiments of the present invention.

The simplicity and low cost of a GASMAS instrument makes it a suitable tool for quality control of food packages both in-line and for point measurements. A future "in-line" laser spectroscopy would make it possible to evaluate non-intrusively if food deterioration has taken place over time, and whether the oxygen is "consumed" in a tight modified atmosphere package.

The apparatus 100 in FIG. 1 may be placed in-line within a product manufacturing chain devised for packaging or products in sealed packages. The apparatus 100 may thus be placed in connection with for example a conveyor belt for transportation of food products subsequent to filling and sealing of the food products. The apparatus 100 would then be useable for measurements on each of the food products, or a selection thereof, when transported between filling and sealing and bulk packaging. The apparatus 100 may be integrated with or standalone with respect a filling machine and/or packaging machine.

The apparatus 100 may assess the sealed packages without contacting the packages and instead detect the gas inside the packages from a remote distance [Ref. 3]. This is advantageous as the speed of detection may be increased.

Results from measurements shows the feasibility of the GASMAS technique as a powerful tool for studying the gas composition as a tool for quality assurance of liquid food products and carton food packaging, performed non-intrusively and over time. The experiments indicate that the GASMAS technique can be used for an important problem of securing food safety through monitoring the quality of liquid food products in modified or "air tight" packages at different steps in the food supply chain and at different times after packaging. Measurements on high quality orange juice packages with modified atmosphere illustrate the possibility to non-intrusively monitor the oxygen content and the water vapour content in liquid food packaging over time. In addition, the measurements indicate a possibility to measure package integrity or tightness non-intrusively based on gas composition measurements.

The present invention has been described above with reference to specific embodiments. However, other embodiments than the above described are equally possible within the scope of the invention. The product in the package maybe liquid or solid. Different method steps than those described above, performing the method by hardware or software, may be provided within the scope of the invention as defined by the appended claims. The different features and steps of the invention may be combined in other combinations than those described. The scope of the invention is only limited by the appended patent claims.

REFERENCES

[1] M. Lewander, Z. G. Guan, L. Persson, A. Olsson and S. Svanberg, Food Monitoring Based on Diode Laser Gas Spectroscopy, Appl. Phys. B 93, 619 (2008)
[2] S. Svanberg, Atomic- and Molecular Spectroscopy—Basic Aspects and Practical Applications, 4th edition (Springer, Heidelberg 2004).
[3] Z. G. Guan, M. Lewander, R. Grönlund, H. Lundberg, S. Svanberg, Gas analysis within remote porous target using LIDAR multi-scattering techniques, Appl. Phys. B 93, 657-663 (2008).
[4]. Persson, L. Andersson, M. Cassel-Engquist, M. Svanberg, K. Svanberg, S. Gas monitoring in human sinuses using tunable diode laser spectroscopy, J. Biomed. Opt. 2007; 12;054001.

The invention claimed is:

1. An apparatus for assessment of a gas composition in a sealed packaging, comprising:
at least one laser source for emission of laser light at a wavelength substantially the same as an absorption wavelength of at least one gas in said gas composition, and said at least one laser source being arrangeable so as to direct said laser light towards said sealed package;
at least one detector arrangeable so as to measure a absorption spectrum signal of light scattered in said sealed packaging and transmitted out from said sealed packaging;
means for estimating a path length covered by said scattered light in said sealed packaging and detected by said at least one detector;
a control unit for calculating a concentration of said at least one gas in said gas composition based on said absorption spectrum signal and said estimated path length.

2. The apparatus according to claim 1, wherein said path length is an interaction path length.

3. The apparatus according to claim 2 wherein said interaction path length is approximated to an equivalent path length.

4. The apparatus according to claim 1, wherein said means for measuring a path length is a second laser source for emission of laser light at a second wavelength substantially the same as an absorption wavelength of at least one reference gas with a known concentration in said gas composition.

5. The apparatus according to claim 4, wherein said concentration is calculated from a ratio between said at least one gas and said at least one reference gas with a known concentration.

6. The apparatus according to claim 4, wherein said at least one gas and said at least one reference gas with a known concentration is detected simultaneous by modulating at different frequencies.

7. The apparatus according to claim 4, wherein said reference gas with a known concentration is water vapour.

8. The apparatus according to claim 1, wherein a wavelength modulation technique is used.

9. The apparatus according to claim 8, wherein said wavelength modulation technics done by sinusoidally modulating said wavelength of said emitted laser light and generated harmonics are analyzed.

10. The apparatus according to claim 9, wherein said wavelength is modulated at about 10 kHz.

11. The apparatus according to claim 1, wherein said control unit is configured to determining if a calculated concentration of said at least one gas in said sealed packaging deviates from an expected concentration.

12. The apparatus according to claim 1, wherein said laser light transmitted into said sealed packaging has a wavelength that substantially matches a translucent wavelength window of said sealed packaging.

13. The apparatus according to claim 1, wherein said laser light is spitted between at least two fibers, wherein one fiber is used for transmitting said laser light to said sealed packaging and one fiber is used for measuring the background.

14. A method of assessing a gas composition in a sealed packaging, comprising:
arranging at least one laser source so as to direct a laser light towards said sealed package
emitting a laser light from said at least one laser source at a wavelength substantially the same as an absorption wavelength of at least one gas in said gas composition;
arranging at least one detector so as to detect light scattered in said sealed packaging and transmitted out from said sealed packaging;
measuring an absorption spectrum signal of said light scattered in said sealed packaging and transmitted out from said sealed packaging;
estimating a path length covered by said scattered in said sealed packaging and detected by said at least one detector;
calculating a concentration of said at least one gas in said gas composition based on said measured absorption spectrum signal and said estimated path length.

15. The method according to claim 14, wherein said path length is an interaction path length.

16. The method according to claim 15, wherein said interaction path length is approximated to an equivalent path length.

17. The method according to claim 14, comprising estimating said path length by using a second laser source for emitting laser light at a second wavelength being substantially the same as an absorption wavelength of at least one reference gas with a known concentration in said gas composition.

18. The method according to claim 17, comprising calculating said concentration of said at least one gas from a ratio between said at least one gas and said at least one reference gas with a known concentration.

19. The method according to claim 17, wherein said reference gas with a known concentration is water vapour.

20. The method according to claim 14, wherein said sealed packaging is a modified atmosphere packaging.

21. The method according to claim 14, wherein said sealed packaging is transparent or partly transparent.

22. The method according to claim 14, wherein said seal packaging is translucent for said laser light.

\* \* \* \* \*